US00PP11733P2

(12) United States Plant Patent
Lemon

(10) Patent No.: US PP11,733 P2
(45) Date of Patent: Jan. 2, 2001

(54) VARIETY OF GERANIUM PLANT NAMED 'GLOBAL MERLOT'

(75) Inventor: David Lemon, Lompoc, CA (US)

(73) Assignee: John Bodger and Sons Company, South El Monte, CA (US)

( * ) Notice: Under 35 U.S.C. 154(b), the term of this patent shall be extended for 0 days.

(21) Appl. No.: 09/149,896

(22) Filed: Sep. 8, 1998

(51) Int. Cl.[7] ..... A01H 5/00
(52) U.S. Cl. ..... Plt./332
(58) Field of Search ..... Plt./332

(56) References Cited

U.S. PATENT DOCUMENTS

P.P. 9,351 * 10/1995 Guillou et al. ..... Plt./332
P.P. 10,502 * 7/1998 Lemon ..... Plt./332

* cited by examiner

*Primary Examiner*—Bruce R. Campell
*Assistant Examiner*—Wendy A Baker
(74) *Attorney, Agent, or Firm*—Fulwider Patton Lee & Utecht, LLP

(57) ABSTRACT

The claimed cultivar is characterized by a red purple double floret further characterized by a speckling of white on some of the florets over a medium green cascading mound. Compared to most ivy geraniums the claimed cultivar exhibits high temperature tolerance as well as quick rooting time and increased cutting production with better floret production.

1 Drawing Sheet

BACKGROUND OF THE NEW PLANT

The present invention comprises a new and distinct cultivar of *Pelargonium×peltatum* known by the varietal name 'Global Merlot' (Oglevee No. 4280, Bodger No. 4 GM 304-3). The new variety was discovered in a selective breeding program by David Lemon at Bodger Seeds, Ltd., Lompoc, Calif. The new variety is a selection from the crossing of 'Nicole' (U.S. Plant Pat. No. 7,358) which has early blooming, candy pink flowers and medium green leaves having a very dark zone, with 'Summer Showers' (unpatented) which produces a purple flower.

The new cultivar was first asexually reproduced by cuttings at Oglevee Ltd., located at 152 Oglevee Lane, Connellsville, Pa., 15425 and has been repeatedly asexually reproduced by cuttings at Oglevee Ltd. in Connellsville, Pa. It has been found to retain its distinctive characteristics through successive propagations.

The new cultivar, was grown in a glass greenhouse in Connellsville, Pa., using full light, 60° Fahrenheit night temperature, 68° Fahrenheit day temperature, and grown in a soilless media using a constant fertilizer of 200–250 parts per million of Nitrogen and Potassium, in full light. The described hanging basket was grown from three rooted cuttings placed into a 10 inch hanging basket. Each of the three cuttings were then pinched after four weeks of growth to promote branching. The basket was then in flower 12 weeks after potting the rooted cuttings. Bloom height is 8.0 to 13.0 cm above foliage. Observed number of florets is 7 to 11 per umbel.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings believed to have been potted in a 20 cm pot on approximately Feb. 25, 1998 and flowering on approximately May 20, 1998, under full light in the greenhouse, and color readings were taken in the Oglevee office under 200–220 foot candles of cool white fluorescent using The Royal Horticultural Society of London Colour Chart.

THE PLANT

Classification:
- *Botanical.*—*Pelargonium×peltatum.*
- *Commercial.*—Ivy Geranium 'Global Merlot'.

Form: Medium cascading mound habit.
- *Height.*—13–14 cm above media.
- *Growth.*—Cascading mound habit.
- *Advantages.*—Presents a uniform cascading hanging basket; quick rooting.

Foliage: Medium green; Stalked leaf attachment.

Leaves:
- *Size.*—6.5–8.0 cm across when fully expanded.
- *Shape.*—Reniform with cordate base.
- *Margin.*—Pedately lobed.
- *Texture.*—Pubescent; Leathery.
- *Color.*—Top: Green Group 137A. Bottom: Green Group 137C. Zone: Greyed-Purple Group 187B.
- *Ribs and veins.*—Palmate venation. Color: Yellow-Green Group 144A.

Petioles:
- *Length.*—4.5–5.5 cm.
- *Color.*—Yellow-Green Group 144A.

Stem:
*Color.*—Yellow-Green Group 144A.
*Internode length.*—2.5–3.5 cm.

THE BUD (UMBEL)

(This information refers to bud size and shape subsequent to elongation but before florets are fully open).

Shape: Elliptical cluster. This information refers to the entire cluster of buds or umbel. Individual bud shape is also elliptical or oval. Number of buds per cluster is 10–12.
Size: 3.0–3.5 cm across.

INFLORESCENCE

Blooming habit: Continuous blooming; Double florets.
Borne: Umbel; Florets on pedicel; Pedicel on peduncle; 5.0–7.5 cm above foliage.
Closed florets: Bud Size: 1.5 cm.
Size: Fully Open Bloom: 5.0–8.5 cm across.
Open florets:
*Form.*—Flat; Ruffled.
*Color.*—Top: Base is Red-Purple Group 59A with veining of Greyed-Purple Group 187A; color is so dark and velvety it appears to reflect Red-Purple Group 59B when tilted to the light. Bottom: Red-Purple Group 59A at edge with Red-Purple Group 59A and White speckles on petal giving an overall appearance of Red-Purple Group 59C. Eye: None.
*Petals.*—15–18 in number.
*Size.*—5.0–5.3 cm across at the widest point.
*Texture and appearance.*—Velvet texture; From a distance deep rich burgundy velvet like flowers above medium green foliage.
Petaloids:
*Quantity.*—1–2 petaloids.
*Shape.*—Twisted; Irregular.
*Color.*—Top: Red-Purple Group 59A. Bottom: Red-Purple Group 59A at edge with Red-Purple Group 59A and White speckles at center of the petal.
Pedicel:
*Length.*—2.7–3.2 cm.
*Color.*—Yellow-Green Group 144A.
Peduncle:
*Length.*—8.5–9.0 cm.
*Color.*—Yellow-Green Group 144A.

Persistence:
*Disease resistance.*—No known special disease resistence compared with other Geraniums.
*Lasting quality.*—Holds up well in high temperatures and does not exhibit edema as quickly as most ivy varieties; Blooming is continuous; Exhibits enhanced bud replacement.

REPRODUCTIVE ORGANS

Stamens:
*Anthers.*—Length: 2.0–3.0 mm.
*Filaments.*—Length: 1.0 cm. Color: White.
*Pollen.*—Golden orange.
Pistils:
*Number.*—1.
Length.—1.0–1.2 cm.
*Stigma.*—Color: Burgundy.
*Style.*—Length: 2.0–3.0 mm.
Ovaries:
*Color.*—Pale Green.
*Length.*—7.0 mm.
Fruit: None.

GENERAL CHARACTERISTICS

'Global Merlot' brings a new and unique variety which can replace the old market varieties Yale (U.S. Plant Pat. No. 3,874) and Harvard (U.S. Plant Pat. No. 3,875) both of which exhibit red to dark red flowers, in color. When compared to these varieties, 'Global Merlot' exhibits superior rooting and increased cutting production. 'Global Merlot' will root in 10–14 days instead of the 21 days needed to root the Yale or Harvard ivy varieties. 'Global Merlot' will also yield up to 30 percent more cuttings than Yale or Harvard. At the same time, 'Global Merlot' provides a better floret formation in a controlled plant habit while exhibiting better heat tolerance and less edema susceptibility. When compared to the ivy varieties 'Yale' and 'Harvard', 'Global Merlot' can tolerate 80 degree Fahrenheit to 85 degree Fahrenheit temperatures and not exhibit foliage yellowing or edema, as 'Yale' and 'Harvard' would.

I claim:

1. A new and distinct variety of Geranium plant, substantially as shown and described.

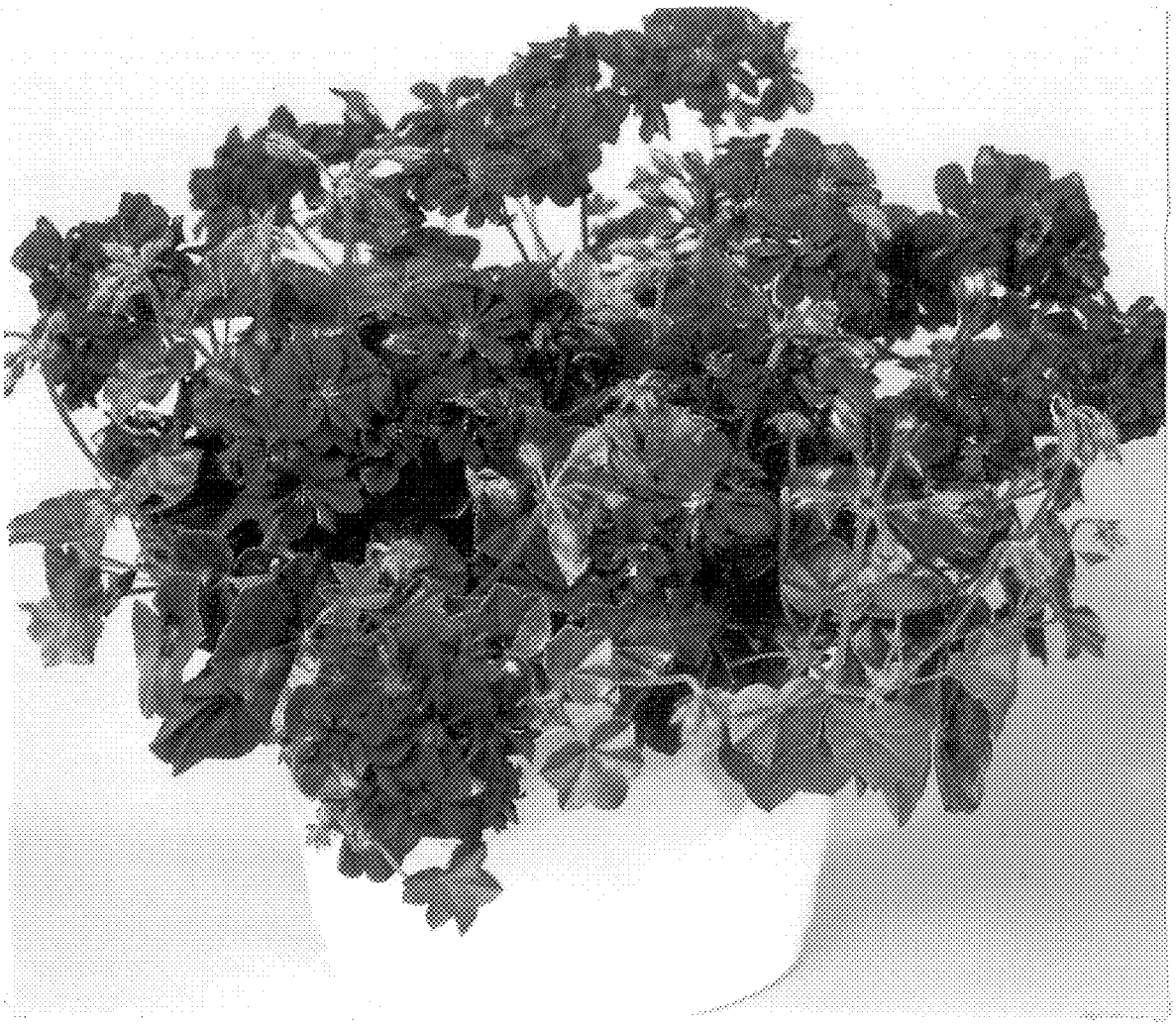

* * * * *